United States Patent [19]

D'Ameila et al.

[11] Patent Number: 6,030,605
[45] Date of Patent: Feb. 29, 2000

[54] BREATH FRESHENING COMPOSITIONS AND METHODS USING THEM

[75] Inventors: Ronald P. D'Ameila, Hicksville, N.Y.; Jack Homcy, Paterson, N.J.; Richard W. Deptula, Budd Lake, N.J.; Daniel Worthy, Succasunna, N.J.; Dorothy A. Panhorst, Morristown, N.J.; Joseph W. Bell, Bethleham, Pa.; Walter Hopkins, Bridgewater, N.J.

[73] Assignee: Nabisco, Inc., Parsippany, N.J.

[21] Appl. No.: 09/227,704

[22] Filed: Jan. 8, 1999

Related U.S. Application Data

[63] Continuation-in-part of application No. 08/832,103, Apr. 3, 1997, abandoned.

[51] Int. Cl.[7] .............................. A61K 9/20; A61K 9/68; A61K 31/315
[52] U.S. Cl. .......................... 424/48; 424/440; 424/441; 424/464; 424/641; 424/642; 424/643
[58] Field of Search ............................ 424/48, 440, 441, 424/464, 641, 642, 643

[56] References Cited

U.S. PATENT DOCUMENTS

| | | | |
|---|---|---|---|
| 4,138,477 | 2/1979 | Gaffar | 424/52 |
| 4,469,674 | 9/1984 | Shah et al. | 424/52 |
| 4,684,528 | 8/1987 | Godfrey | 426/74 |
| 4,758,439 | 7/1988 | Godfrey | 426/74 |
| 4,765,984 | 8/1988 | Vellekoop et al. | 424/441 |
| 4,814,163 | 3/1989 | Barth | 424/49 |
| 4,814,164 | 3/1989 | Barth et al. | 424/49 |
| 5,057,416 | 10/1991 | Chervkuri et al. | 424/48 |
| 5,095,035 | 3/1992 | Eby | 514/494 |
| 5,250,569 | 10/1993 | Godfrey | 514/561 |
| 5,286,748 | 2/1994 | Eby | 514/494 |
| 5,370,881 | 12/1994 | Fuisz | 426/5 |
| 5,405,836 | 4/1995 | Richar et al. | 514/23 |
| 5,409,705 | 4/1995 | Eby | 514/23 |

*Primary Examiner*—Shep K. Rose
*Attorney, Agent, or Firm*—Scully, Scott, Murphy & Presser

[57] ABSTRACT

The present invention is directed towards the use of chewing gums, tablets and lozenges containing a breath freshening composition which comprises a physiologically acceptable zinc compound, an oil, and a non-ionic surfactant, to reduce or eliminate $H_2S$ and $CH_3SH$ in the oral cavity.

15 Claims, 17 Drawing Sheets

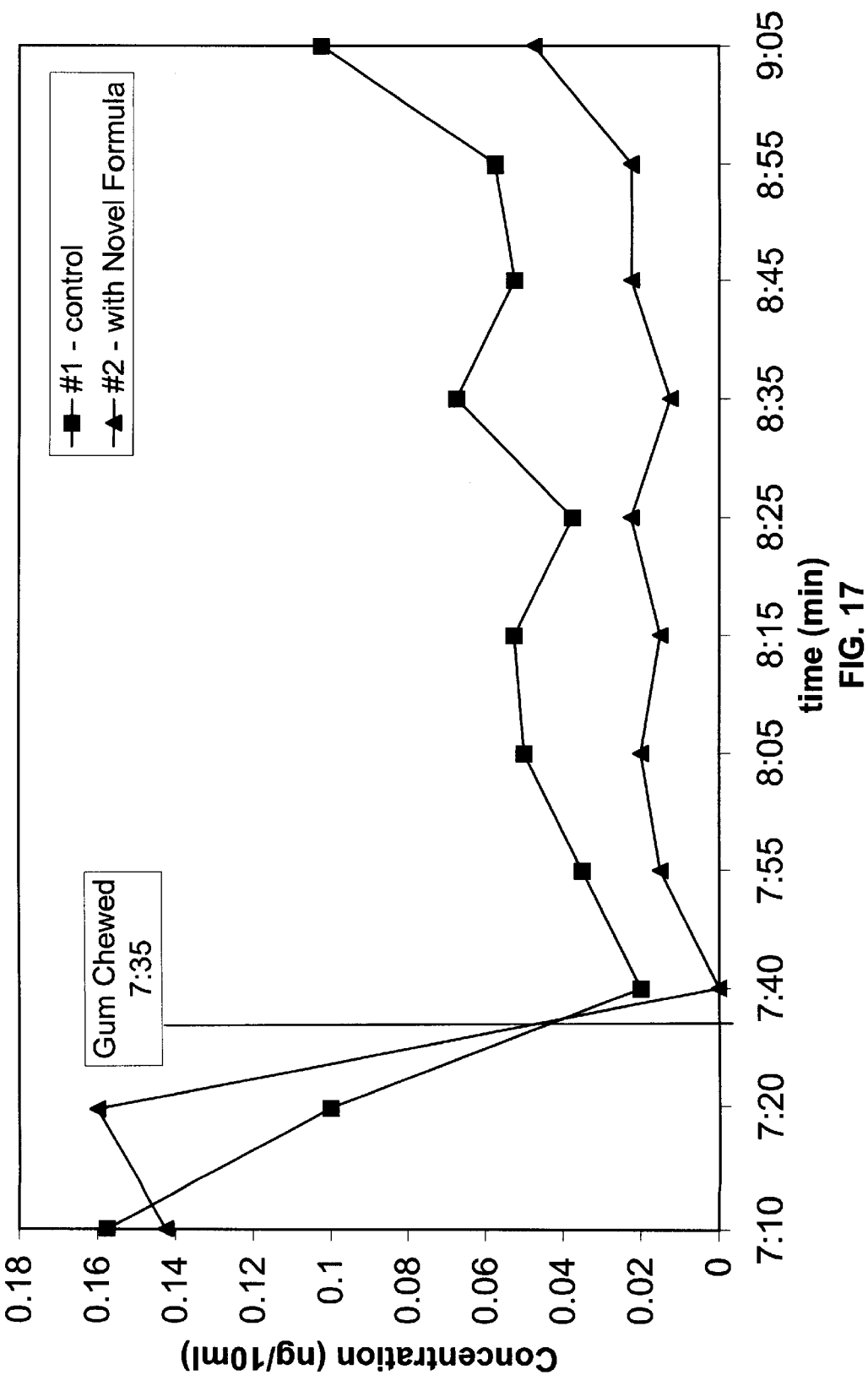

BREATH FRESHENING COMPOSITIONS AND METHODS USING THEM

This application is a continuation-in-part of application Ser. No. 08/832,103, filed Apr. 3, 1997, now abandoned.

BACKGROUND OF THE INVENTION

Volatile sulfur compounds, mainly $H_2S$ and $CH_3SH$, generated in the human oral cavity have been documented to be the primary cause of breath malodor. Generally, the presence of these compounds is most noticeable after long periods of reduced saliva flow and abstinence from food or liquids, resulting in the condition known as "morning breath." Breath malodor can also arise after ingesting various foods such as garlic, cabbage and onions.

Zinc compounds, including zinc salts, have been disclosed in the literature as the active ingredient in mouthwashes, rinses and toothpaste to ameliorate breath malodor.

For example, U.S. Pat. No. 4,814,164, discloses a solid oral formulation comprising a zinc compound, an ionone ketone terpene derivative and preferably a mint flavor as the active ingredient.

A clear aqueous composition useful as a mouthwash comprising a zinc compound complexed to an anionic polymer via a carboxylic moiety is disclosed in U.S. Pat. No. 4,992,259.

Other oral compositions containing zinc compounds including toothpastes, mouthwashes, tablets and lozenges, have been disclosed in U.S. Pat. Nos. 4,138,477, 4,325,939, and 4,469,674.

SUMMARY OF THE INVENTION

The present invention is directed towards a breath freshening composition which can be used in different confectionery products such as hard candies, pressed mints, tablets, lozenges and chewing gums.

One aspect of the present invention is directed towards the use of a breath freshening composition comprising a physiologically acceptable compound of a divalent metal such as zinc and/or copper, an oil, and a surfactant.

Another aspect of the present invention is directed towards the use of comestible products for humans, such as tablets, lozenges, chewing gums, hard candies, and pressed mints, or comestible products for animals, such as dog biscuits, wherein the comestible products contain a breath freshening composition of the present invention.

The present invention is further directed towards the use of chewing gums, tablets, lozenges, hard and chewy candies and pressed mints which contain a breath freshening composition that has the ability to reduce or eliminate the volatile sulfur compounds which cause bad breath.

One advantageous aspect of the present invention is that in previous products it has often been necessary to employ such a high amount of zinc, to counteract the malodor, that the taste of the zinc became unacceptably pronounced thereby rendering the product unattractive to the consumer. By contrast, the present invention achieves superior breath freshening (malodor control) with lesser amounts of zinc, thereby providing a breath freshening product which does not exhibit an unattractive zinc taste.

BRIEF DESCRIPTION OF THE DRAWINGS

FIGS. 1–17 are graphs showing concentration of $H_2S$ and $CH_3SH$ versus time in the breath of subjects tested.

DETAILED DESCRIPTION OF THE INVENTION

Figure 1:
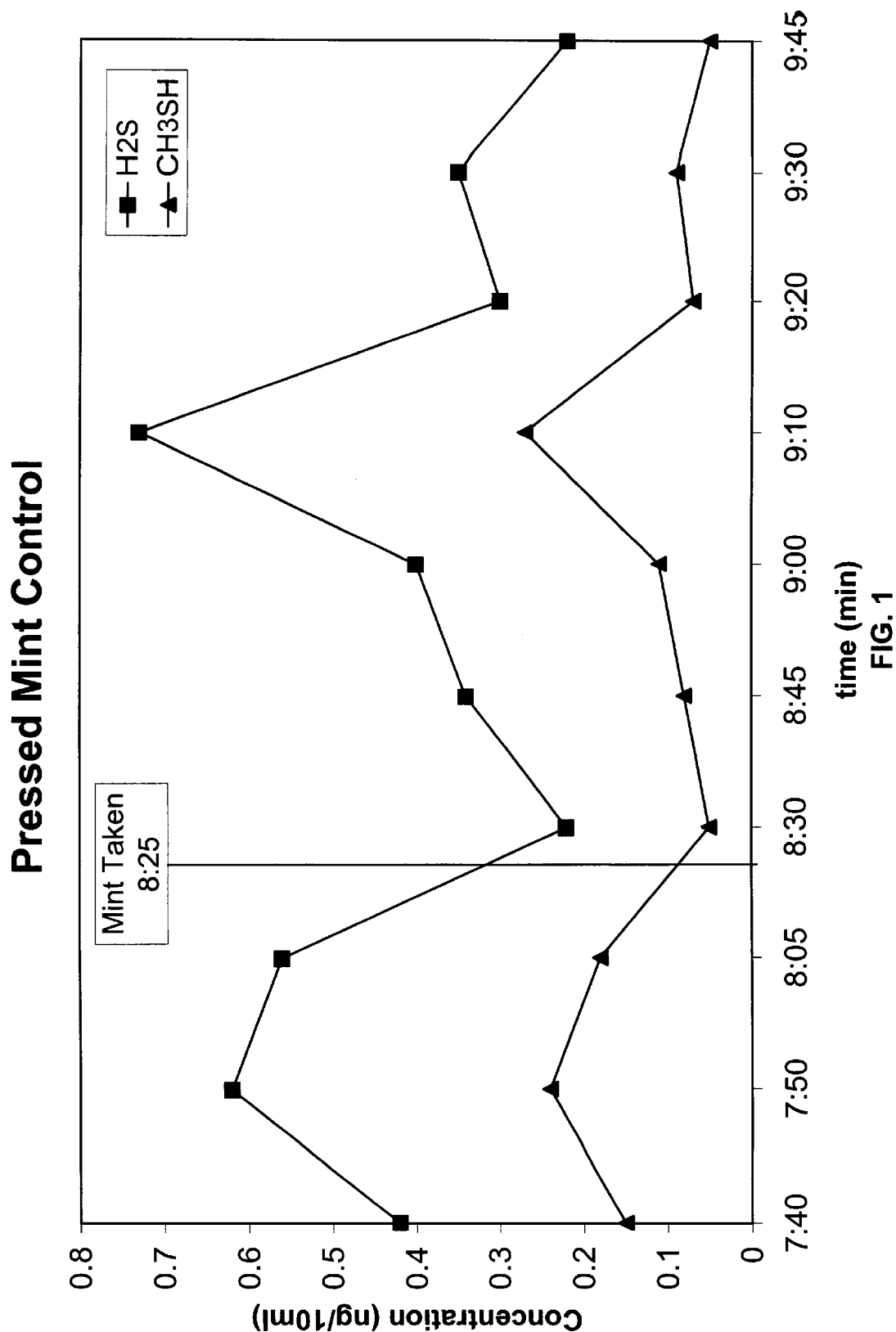
Figure 2:
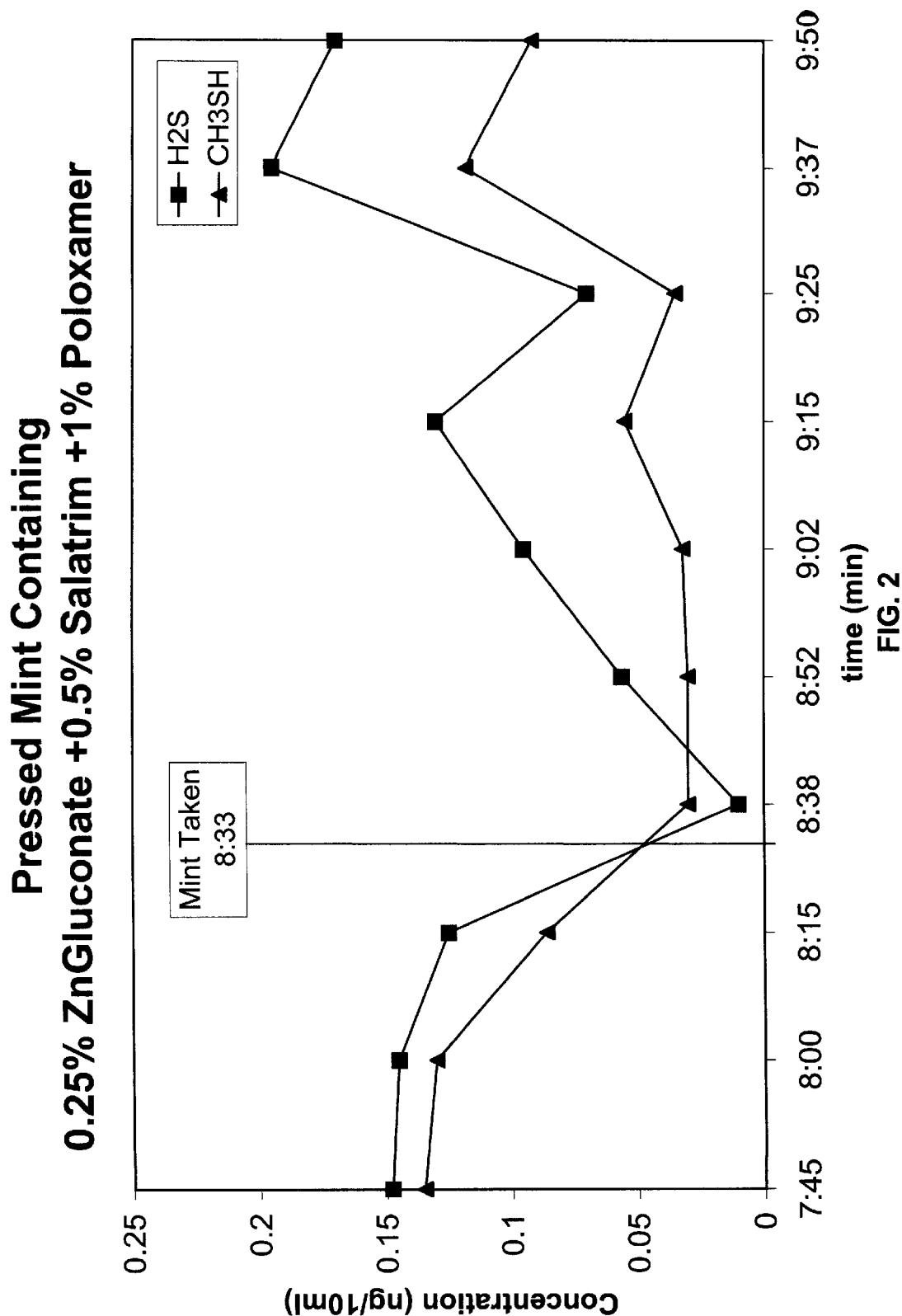
Figure 3:
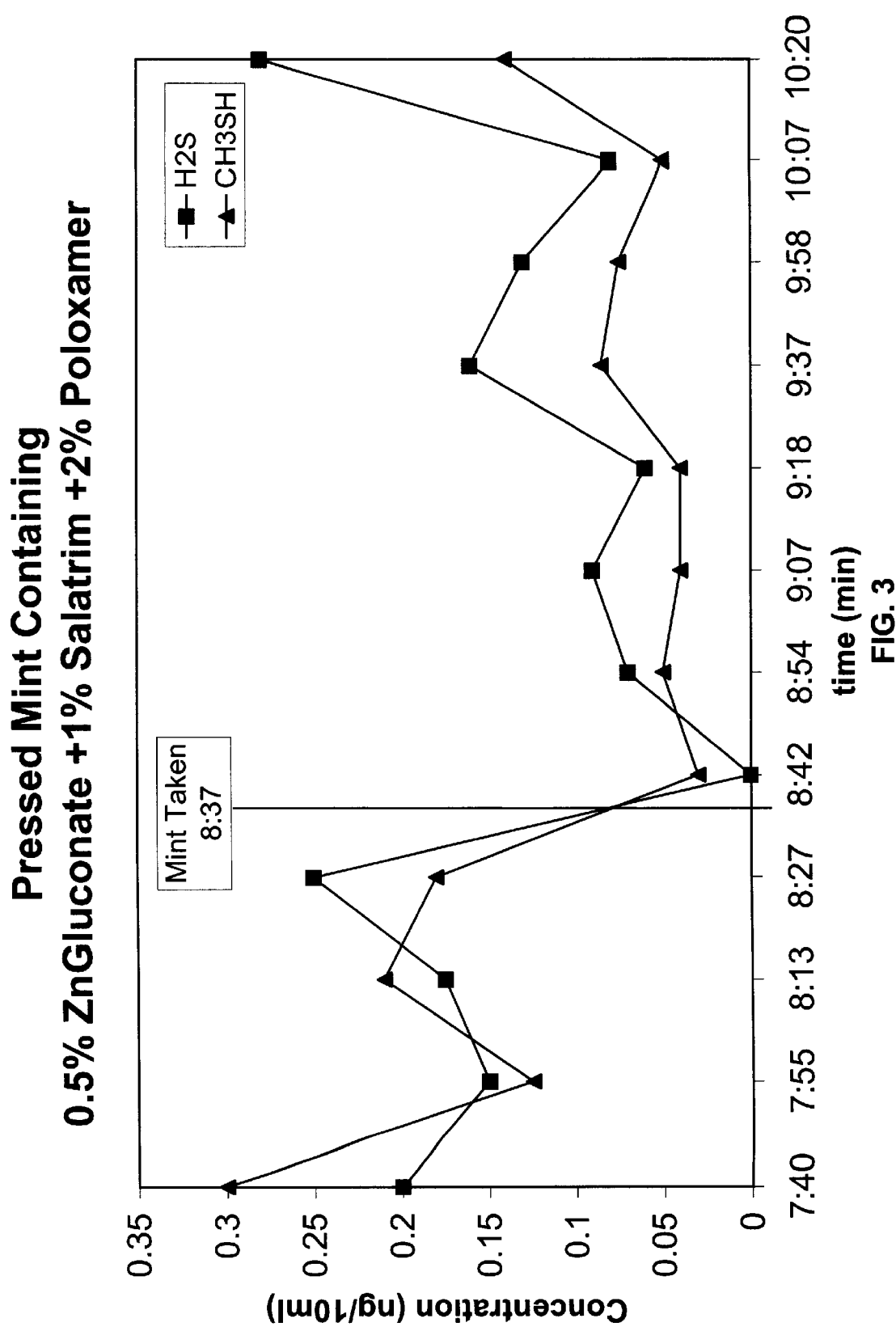
Figure 4:
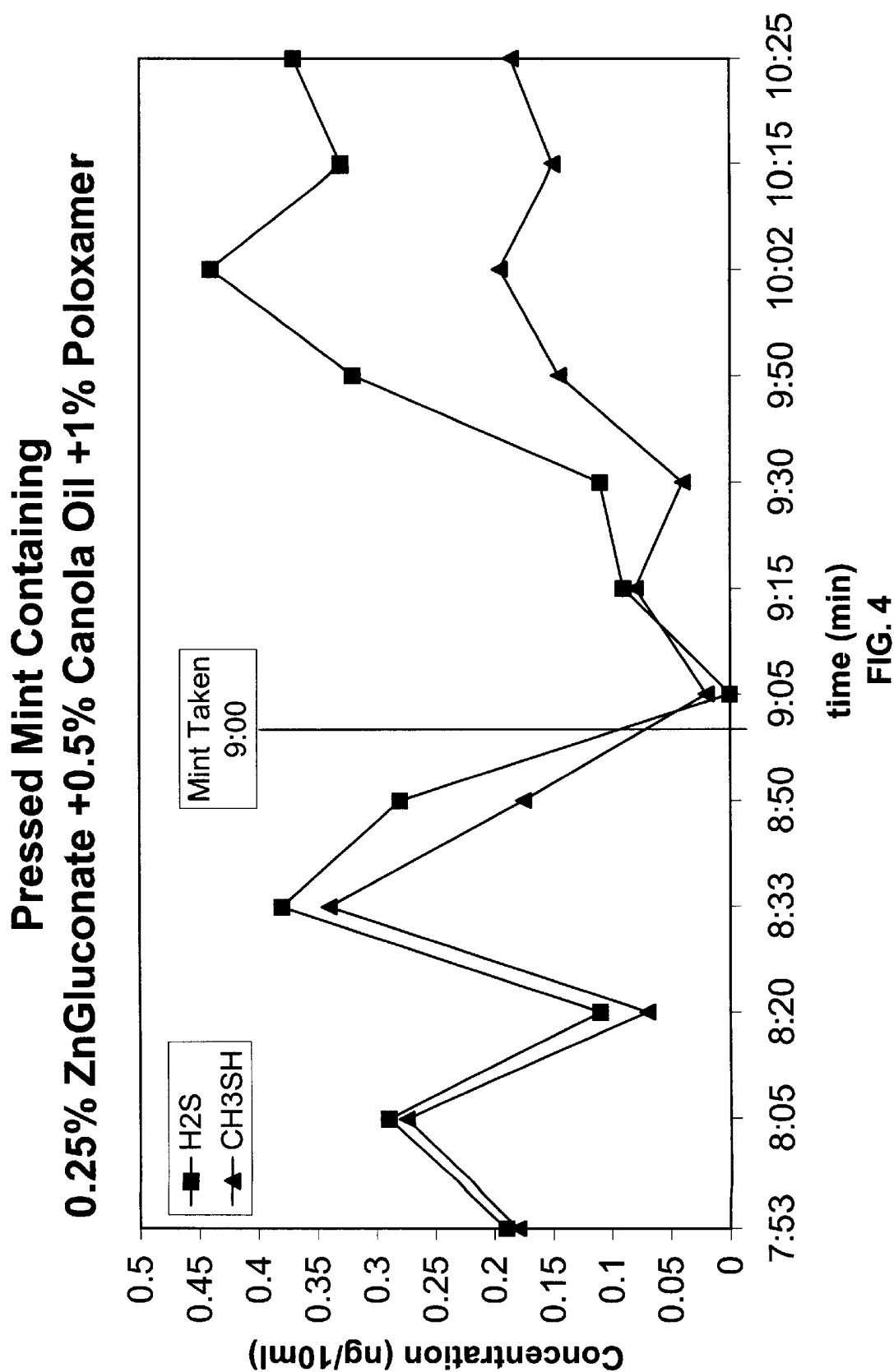
Figure 5:
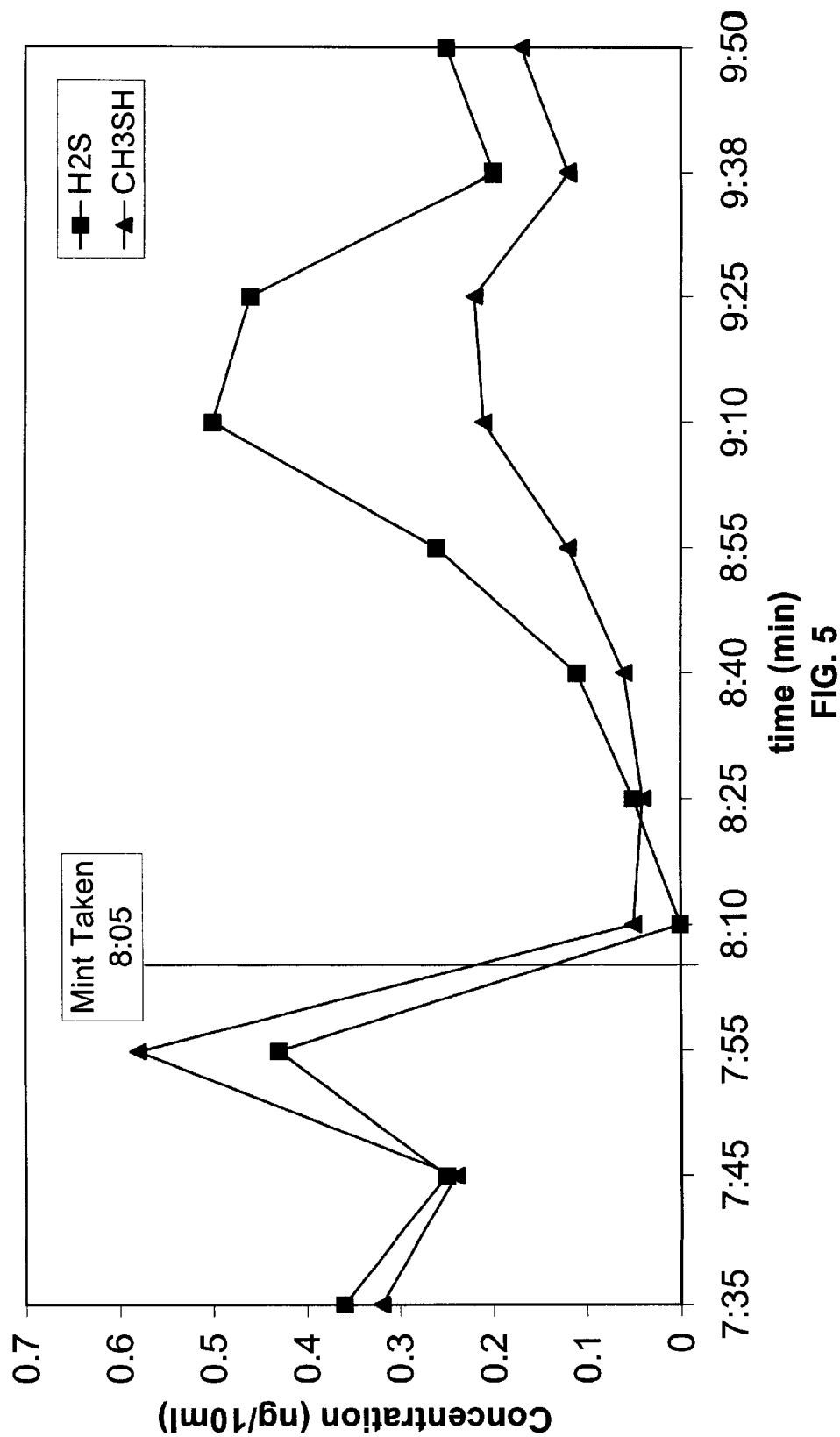
Figure 6:
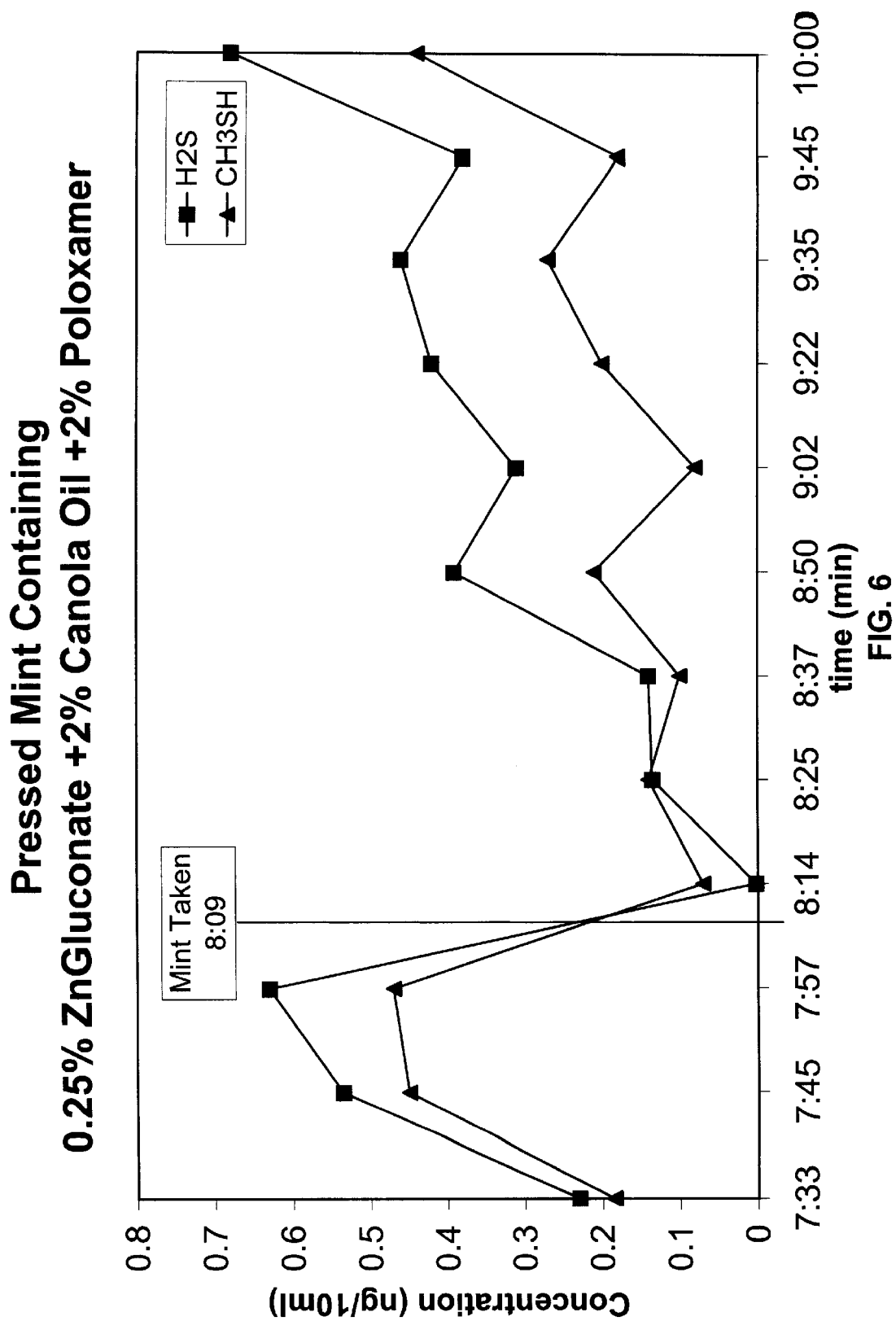
Figure 7:
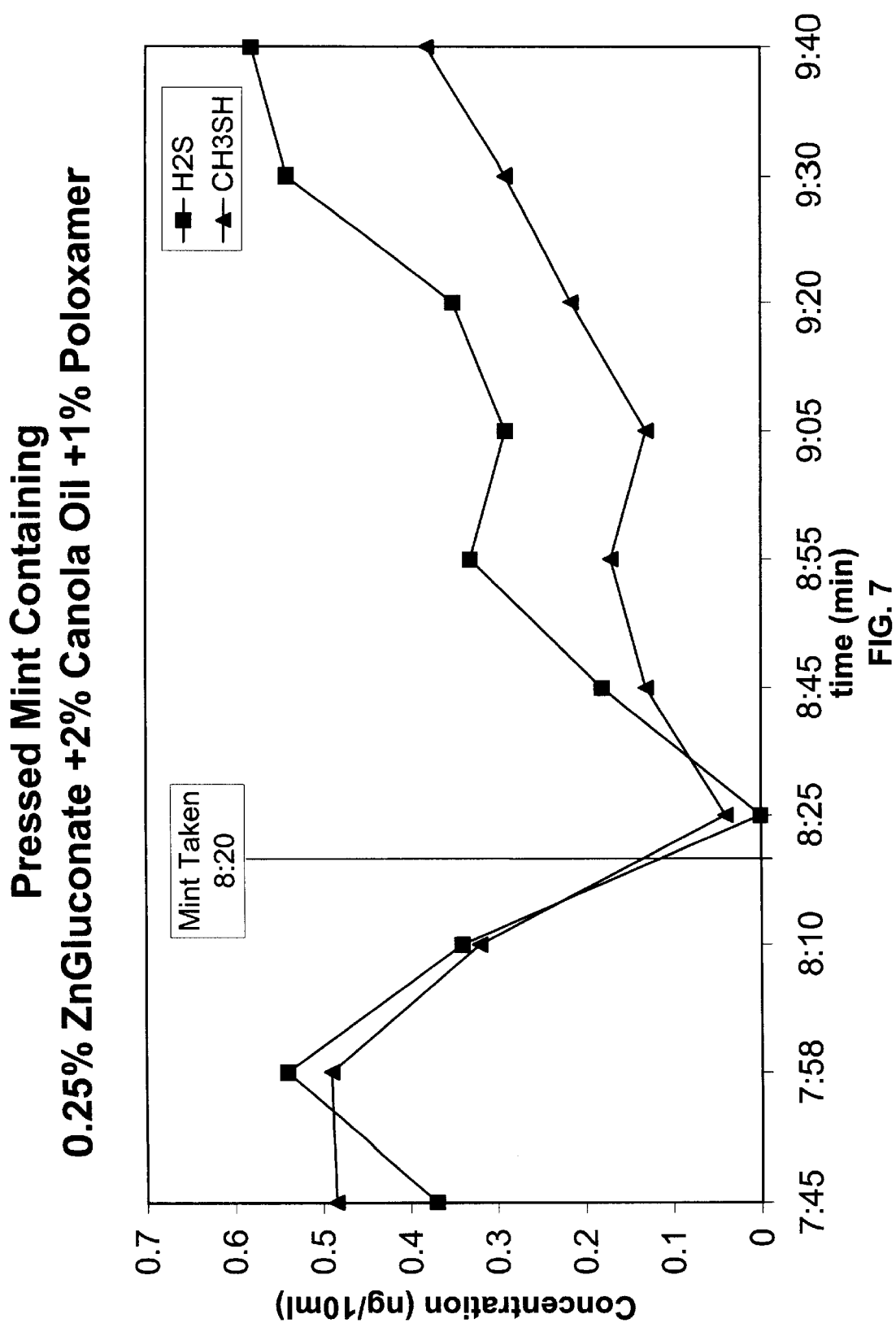
Figure 8:
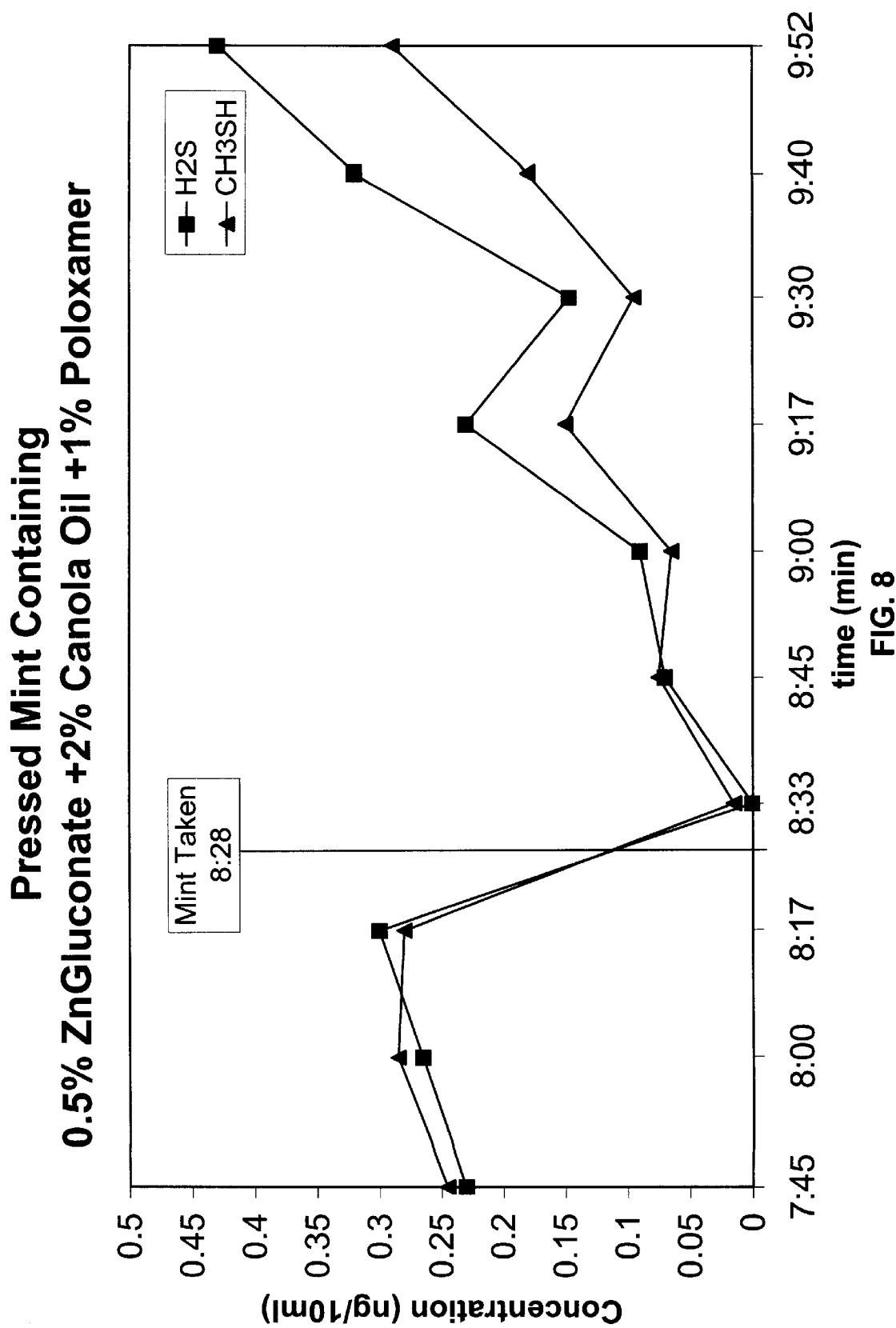
Figure 9:
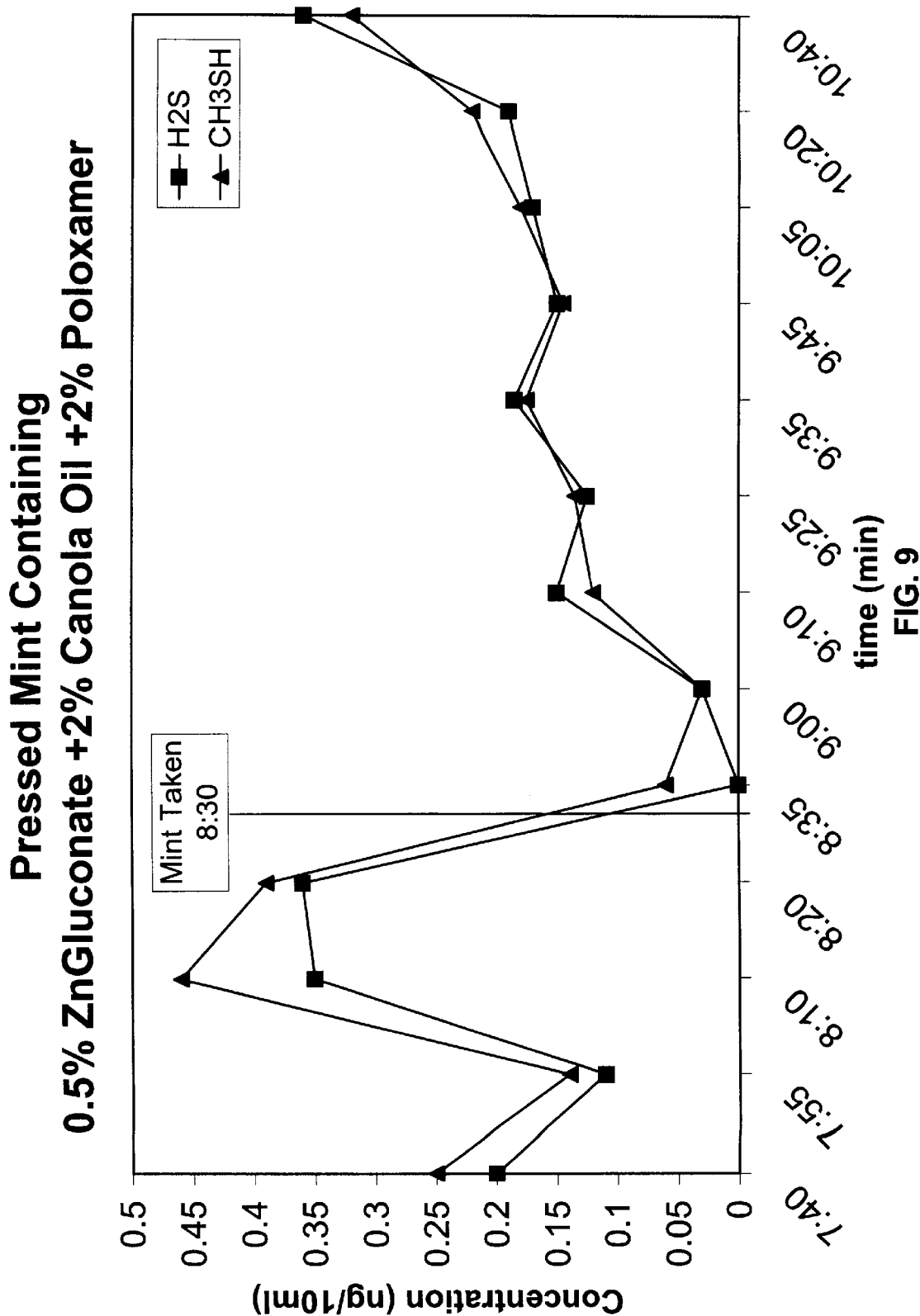

The present invention is directed to a method of reducing or eliminating $H_2S$ and $CH_3SH$ present in the oral cavity, comprising masticating in the oral cavity a comestible product which contains a breath freshening composition comprising a pharmaceutically acceptable compound of a divalent metal, an oil, and a surfactant. Suitable comestible products include tablets, lozenges, chewing gums, hard and chewy candies, pressed mints, and dog biscuits, which contain a breath freshening composition of the present invention.

The term "masticating" includes operations by which an edible product is wholly or partially consumed while it is being held in the mouth, such as by chewing, sucking, or dissolving. Holding the product in the mouth for longer periods of time is associated with greater reduction of $H_2S$ and $CH_3SH$ present in the oral cavity, and with more prolonged periods of time before the $H_2S$ and $CH_3SH$ return to previous levels in the oral cavity. Suitably effective periods of time range from 3–5 minutes, up to 20–30 minutes.

It has been found that the practice of this method not only reduces or eliminates $H_2S$ and $CH_3SH$ present in the oral cavity but also retards the return of those compounds in the oral cavity for a surprisingly prolonged period of time.

The divalent metal compounds of the present invention may include any physiologically acceptable compound effective to ameliorate oral malodor, including the water soluble and sparingly water soluble organic and inorganic salts of such divalent metals.

The preferred divalent metals are zinc and copper. Examples of suitable zinc salts include zinc stearate, zinc acetate, zinc gluconate, zinc lactate, zinc ammonium sulfate, zinc chromate, zinc citrate, zinc dithionate, zinc fluosilicate, zinc tartrate, zinc formate, zinc iodide, zinc nitrate, zinc phenol sulfonate, zinc salicylate, zinc sulfate, zinc succinate, zinc glycerophosphate and the zinc halides, such as zinc chloride. The preferred zinc compounds for use in accordance with the present invention are zinc gluconate and zinc lactate.

Suitable copper salts include the copper analogs of the aforementioned zinc compounds.

The total amount of divalent metal compound(s) present in the breath freshening composition should be 0.5% to 90% by weight, preferably 2% to 70% by weight, of the composition (by weight of the divalent metal(s)).

The oil component of the present invention includes any physiologically acceptable oil, particularly any edible vegetable oil. As used herein, the term "vegetable oil" includes any edible naturally occurring vegetable oil, which as is known are triglycerides of fatty acids in which the acyl portions generally contain 8 to 24 carbon atoms and zero to three carbon-carbon double bonds. The term "vegetable oil" as used herein also includes naturally occurring oils which have been purified and/or modified, for instance by bleaching or by partial or complete hydrogenation. Oils useful in this invention are liquid at ambient temperatures i.e. 40° F.–90° F. One preferred example of an oil is canola oil. Other suitable oils include the low calorie oil based on short and long chain fatty acids which is known by its trade designation "SALATRIM" (Cultor). Other suitable oils include medium chain triglyceride compounds of capric and caprylic acids. An example is Liponate GC from Lipo Chemicals. Suitable oils also include soybean oil and corn oil. Other acceptable oils will be familiar to one of ordinary skill in the art.

The oil component is present in the breath freshening compositions in amounts from 1% to 90% by weight of the composition, preferably 20% to 70% by weight of the composition.

The surfactant component of the breath freshening compositions of the present invention includes a surfactant or a mixture of surfactants. Suitable surfactants include nonionic, anionic, amphoteric and cationic surfactants.

Examples of suitable non-ionic surfactant include:

poly($C_2$–$C_4$-alkoxy) esters, and particularly polyoxyethylene ("PEG") esters, of $C_8$–$C_{20}$ fatty acids, such as polyethyleneglycol oleate and polyethyleneglycol stearate;

$C_4$–$C_{20}$ alkyl polyglycol ether carboxylates of $C_8$–$C_{20}$ carboxylic acids including the compounds described in U.S. Pat. No. 4,130,636, which is incorporated herein by reference;

poly($C_2$–$C_4$-alkoxy) esters, and particularly polyoxyethylene esters of sorbitan, such as those described in U.S. Pat. Nos. 3,639,563 and 3,947,570, which are incorporated herein by reference;

poly($C_2$–$C_4$-alkoxylated) and particularly poly (propoxylated) $C_1$–$C_{20}$, alcohols such as cetyl alcohol, including those described in U.S. Pat. No. 2,677,700, which is incorporated herein by reference; and polyethylene glycols, commonly referred to as PEG, and the like.

Other suitable surfactants include block copolymers comprising a congeneric mixture of conjugated polyoxypropylene and polyoxyethylene compounds having as a hydrophobe, a polyoxypropylene polymer of at least 1200 molecular weight, such as those described in U.S. Pat. Nos. 4,343,785, 4,465,663, 4,511,563 and 4,476,107, which are incorporated herein by reference.

These polymers are prepared by adding the required number of moles of propylene oxide to the two hydroxyl groups of propylene glycol to form a hydrophobic base and then adding ethylene oxide to both ends of the hydrophobic base to form hydrophilic polyoxyethylene groups of controlled length. Various species of such polymers, including those defined above as useful in the invention, are available commercially from BASF/Wyandotte Chemicals Corporation of Wyandotte, Mich. under the trademark "Pluronic."

Especially preferred are the commercially available surfactant which include the polyoxyethylene-polyoxypropylene block copolymers such as Pluronic F108 and F127 (BASF) and polysorbates such as Tween 40 and 80 (Hercules).

Most preferred are the non-ionic polyoxypropylene-polyoxyethylene block co-polymers or poloxamers. These polymers have a molecular weight range of 500 to 30,000 and are of the general formula:

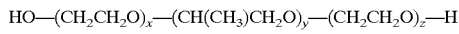

HO—($CH_2CH_2O$)$_x$—($CH(CH_3)CH_2O$)$_y$—($CH_2CH_2O$)$_z$—H wherein x is 2–128, y is 16–67 and z is 2–128.

Suitable anionic, amphoteric and cationic surfactants which are suitable for incorporation into comestible products are well known in this field from published sources and from the knowledge of those skilled in this art.

The surfactant is present in the breath freshening compositions of the present invention from about 1% to 90% by weight, preferably 10% to 70% by weight.

The breath freshening compositions of the present invention are prepared by thoroughly mixing together the divalent cationic component, the oil, and the non-ionic surfactant. Alternatively, the three components can be added separately, directly to the comestible product in which they are to be provided to the consumer.

Another embodiment of the present invention contemplates the incorporation of the breath freshener compositions of the present invention into chewing gums and solid oral carriers such as slow dissolving tablets or lozenges.

In one aspect of this embodiment, the breath freshening compositions are incorporated into otherwise typical chewing gum compositions manufactured by conventional techniques.

Chewing gums of the present invention comprise the gum base itself, and optionally one or more of solvents, plasticizers, sweeteners, flavorants and/or colorants. Several formulations are possible, depending upon the type of gum desired, i.e., sugar containing or sugarless chewing gums, conventional chewing gums or bubble gums.

The amount of gum base employed will vary greatly depending on various factors such as the type of base used, consistency desired and other components used to make the final product. In general, gum base in amounts of about 5% to about 50% by weight of the final chewing gum composition are acceptable for use in the chewing gum compositions, preferred amounts thereof being about 15% to about 25% by weight.

The gum base may be any water-insoluble gum base known in the art. Illustrative examples of suitable polymers in gum bases include both natural and synthetic elastomers and rubbers. For example, those polymers which are suitable in gum bases include, without limitation, substances of vegetable origin such as natural rubber, chicle, jelutong, gutta percha and crown gum. Further examples of gum bases include rosins, such as comarone resin, pontianak resin, copal gum, kauri gum, dammar gum, sweet bay gum, spruce gum, and balsams.

Conventional chewing gum bases that may be obtained from commercial suppliers are generally suitable.

Additional materials which are also suitable chewing gum base materials include synthetic elastomers such as butadiene-styrene copolymers, isobutylene-isoprene copolymers, polyethylene, polyisobutylene, polyvinyl acetate, and copolymers of vinyl acetate, and mixtures thereof.

The gum base composition may contain elastomer solvents to aid in softening the elastomer component. Such elastomer solvents may comprise methyl, glycerol or pentaerythritol esters of rosins or modified rosins, such as hydrogenated, dimerized or polymerized rosins, or mixtures thereof. Examples of elastomer solvents suitable for use herein include the pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene; and mixtures thereof. The solvent may be employed in an amount ranging from about 10% to about 75% and preferably about 45% to about 70% by weight of the gum base.

The gum base can also contain any of a variety of ingredients such as plasticizers or softeners such as lanolin, stearic acid, sodium stearate, potassium stearate, glyceryl triacetate, propylene glycol, glycerol, acetylated monoglyceride, glyceryl diacetate, lecithin, fatty acids, glycerine and the like and/or waxes, for example, natural waxes, petroleum waxes, such as paraffin waxes and microcrystalline waxes, to obtain a variety of desirable textures and consistency properties. These individual additional materials are generally employed in amounts of up to about 30% by weight and preferably in amounts of from about 3% to about 20% by weight of the gum base.

The chewing gum composition may additionally include conventional additives such as emulsifiers such as lecithin and glyceryl monostearate; and additional fillers such as dicalcium phosphate, tricalcium phosphate, aluminum hydroxide, magnesium hydroxide, alumina, aluminum silicates, calcium carbonate, and talc and combinations thereof. These fillers may be used in the gum base in various amounts. Preferably the amount of fillers when used will vary from about 4 to about 30% by weight of the chewing gum.

Another aspect of this embodiment contemplates the incorporation of a breath freshening composition into a solid carrier such as a tablet or lozenge.

The solid carrier is sugar or a water soluble polyhydric alcohol (polyol) such as mannitol, xylitol, sorbitol, maltitol, a hydrogenated starch hydrolysate ("Lycasin"), hydrogenated glucose, hydrogenated disaccharides, and/or hydrogenated polysaccharides, as the major ingredient, in an amount of about 85–98% by weight of the total carrier. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and the lozenges. Suitable lubricants include vegetable oil such as coconut oil, magnesium stearate, aluminum stearate, talc, starch and Carbowax.

Lozenge formulations contain about 2% hydrocolloid as a barrier agent to provide a shiny surface as opposed to a tablet which has a smooth finish.

The lozenge or tablet may optionally be coated with a coating material such as waxes, shellacs, carboxymethyl cellulose, polyethylene/maleic anhydride copolymer or Kappa-carrageenan, to further increase the time it takes the tablet or lozenge to dissolve in the mouth. The coated tablet or lozenge is slow dissolving, providing a sustained release rate of the active ingredients of about 3 to 5 minutes.

The breath freshening compositions of the present invention are incorporated into a lozenge or tablet by conventional mixing and tabletting techniques known in this field.

The present embodiment further contemplates the optional inclusion of a sweetener, flavorant, or colorant component into the chewing gums, tablets or lozenges containing the breath freshening composition.

The sweetener component comprises any one or more sweeteners known in the art, including both natural and artificial sweeteners. The sweetener may be chosen from a wide range of materials, including water-soluble sweeteners, water-soluble artificial sweeteners and dipeptide based sweeteners and mixtures thereof. Thus, sweeteners may be chosen from the following non-limiting list, which includes sugars such as sucrose, glucose, corn syrup, dextrose, invert sugar, fructose and mixtures thereof; saccharine and its various salts such as the sodium or calcium salt; cyclamic acid and its various salts such as the sodium salt; free aspartame; dihydrochalcone sweetening compounds; glycyrrhizin; Stevia rebaudiana (Stevioside); monellin, thaumatin, Sucralose, isomaltitol, neosugar, lactitol, polydextrose, tagatose, and maltitol; and sugar alcohols such as sorbitol, sorbitol syrup, mannitol, xylitol, chalcone and the like. Also contemplated as a sweetener is the nonfermentable sugar substitute hydrogenated starch hydrolysate (also known as Lycasin) which is described in U.S. Pat. No. Re. 26,959. Also contemplated is the synthetic sweetener 3,6-dihydro-6-methyl-1-1,2,3-oxathiazin-4-one-2,2-dioxide, particularly the potassium (Acesulfame-K), sodium and calcium salts thereof as described in German Patent No. 2,001,017.7. Sorbitol is the preferred sweetening and bulking agent.

The amount of sweetener included is an amount effective to provide the desired degree of sweetness and bulk, generally 0.001 to 70 wt. % of the chewing gum, tablet or lozenge.

Suitable flavorants include both natural and artificial flavors and mints, such as oil of peppermint, menthol, oil of spearmint, vanilla, oil of cinnamon, oil of wintergreen (methyl salicylate), and various fruit flavors, including but not limited to lemon oil, orange oil, grape flavor, lime oil, grapefruit oil, apple, apricot essence, and combinations thereof. The flavorings are generally utilized in amounts that will vary depending upon the individual flavor, and may, for example, range in amounts of about 0.5% to about 3% by weight of the chewing gum, tablet or lozenge.

Colorants can be present in the chewing gums, tablets or lozenges of the present invention. Examples include pigments such as titanium dioxide, natural food colorants such as beta carotenes, betanin, turmeric, and other dyes suitable for food, drug and cosmetic applications known as F.D. & C. dyes, and the like. The materials may be incorporated in amounts of up to about 1% by weight, preferably up to about 6% by weight of the chewing gum, tablet or lozenge.

When the breath freshening compositions of the present invention are incorporated into hard candies, pressed mints, lozenges or tablets, the divalent metal compound is present in an amount from about 0.1 to 0.75% by weight, the oil in an amount from about 0.1 to 3% by weight, and the surfactant in an amount from about 0.1 to 3% by weight.

A representative formulation for a hard candy embodying the composition of the present invention is as follows:

| | |
|---|---|
| Sorbitol | 94–98 wt. % |
| Magnesium Stearate | 0.6–0.8 |
| Colorants | 1.5–4. |
| Flavor | <1. |
| Sweetener | 0.1–0.2 |
| Breath freshening composition of the present invention | 0.1–4.0 |

The present invention will be further illustrated with reference to the following examples which will aid in the understanding of the present invention, but which are not to be construed as limitations thereof.

The instrumentation and test procedures employed in the examples which appear below and in obtaining the data reported herein, were as follows:

GAS CHROMATOGRAPH SET-UP AND CALIBRATION

A Hewlett Packard 5890 gas chromatograph was modified for the breath sampling work. The injector was equipped with a 10 port Valco sampling valve ordered from Supelco Inc. Bellefonte, Pa. (cat#2-2981M) and a 16.5'×⅛" O.D. Teflon sample loop. With a ¹⁄₁₆" I.D., this tube has a volume of 10 milliliters. The valve configuration with attached tubes are shown in FIGS. 1A and 1B. The chromatographic column was 25'×⅛" Teflon packed with 5% polyphenol ether (5 ring) and 0.5% phosphoric acid on 40/60 mesh Teflon (Supelco). Condition column at 120° C. overnight. All the tubing, valves and connections in contact with the sulfur compounds were Teflon coated, since glass or metal tend to absorb these compounds making consistent, reliable results difficult to obtain.

The gas chromatograph utilizes a Flame Photometric detector (FPD). Dry compressed air was used as the carrier gas to eliminate the solvent front peak from the chromatogram. Carrier gas flow was 13.3 mls/min, however, since the flowmeter on this GC is calibrated for nitrogen, the flow was set to a 20. mls/min reading to compensate.

The oven temperature profile is 70–100° C. @ 6 degrees/min. 1 min at 70 and 1 min at 100° C. The injector temperature is 100° C. and the detector temperature is 150° C. The total run time is 7.0 minutes with $H_2S$ eluting at 2.1 minutes and $CH_3SH$ eluting at 2.8 minutes. At this rate a sample can be taken every 10–15 minutes. A third peak may appear at times, identified as dimethyl sulfide ($CH_3$—S—$CH_3$), which is not a primary peak of interest and usually represents less than 1% of the total area.

Calibration of the instrument was accomplished using standard gas permeation tubes ordered from VICI Metronics (Santa Clara, Calif.). The tubes which emitted the sulfur compounds at a constant rate ($H_2S$=100 ng/min and $CH_3SH$=65 ng/min), were placed inside a Teflon cylinder (in a 30° C. water bath) and connected to a dry-air source. The concentrations vary with each new set of standards. A soap film flowmeter measured flow and thru calculation the concentration being injected into the GC was determined. The calibration procedure is a multi-level external standard using peak area response.

GAS CONCENTRATION CALCULATION

Permeation tube gas rates: $H_2S = 105$ ng/min $CH_3SH = 55.1$ ng/min.

Calculation: $\dfrac{\text{(gas rate) ng/min}}{\text{(air flow) ml/min}} = \dfrac{\text{ng}}{\text{ml}}$ of gas

BREATH SAMPLING TECHNIQUE

1. Subject is asked not to eat or drink for a period of 12 hours before testing.
2. The morning of the test the subject was to refrain from normal morning oral hygiene (i.e. brushing teeth, using mouthwash, etc.), eating or drinking.
3. For each sample the subject was asked to hold their mouth closed while breathing through the nose, to allow equilibration of mouth air for one minute, and not swallow.
4. After one minute, subject inserted the Teflon sample tube through their tightly closed lips into the mouth to a depth of 2.25 inches. The shoulder of the mouthpiece marked the limit of insertion. The end of the tube was placed toward the back of the mouth over the center of the tongue.
5. During sample withdrawal (about 5 seconds), the subject was asked to stop breathing. A thirty milliliter sample of mouth air was drawn to fill the 10 ml GC sample loop using a 60 ml disposable syringe.
6. The sample tube was removed from the mouth, and the sample was injected into the GC using the switching valve and the run started. Samples were generally taken every 10–15 minutes until the completion of the test. The average test time is 2 hours 30 minutes.

In the following examples, the data readings of the $H_2S$ and $CH_3SH$ content of the subject's breath before the comestible product was taken into the mouth provided a baseline corresponding to the untreated levels of those components. Readings of $H_2S$ and $CH_3SH$ of the subject's breath, taken at intervals of time after the comestible product had been taken, provided a means for monitoring the length of time that elapsed until the $H_2S$ and $CH_3SH$ levels returned to the baseline levels. A longer elapsed time to return to baseline corresponds to greater suppression of malodor.

The data reported in the following examples show that comestible products (here, a pressed mint product and an otherwise conventional chewing gum) containing the combination of zinc salt, edible oil, and nonionic surfactant in accordance with the present invention provide substantial suppression of $H_2S$ and $CH_3SH$ in the oral cavity for prolonged periods of time.

This suppression always significantly exceeded that obtained with a pressed mint control product of identical composition except that the combination of zinc salt, edible oil and nonionic surfactant was not present. The performance of the control pressed mint product is shown in FIG. 1. The vertical line marked with an "x" represents the time at which the product was taken into the mouth. As can be seen, by only 20 minutes later the levels of $H_2S$ and $CH_3SH$ in the oral cavity had returned to the levels they had at the time that the product was initially taken into the mouth.

FIGS. 2 through 9 show the performance of the same pressed mint containing a zinc salt, an edible oil, and a nonionic surfactant, in varying amounts of those three components. As with FIG. 1, the vertical line marked with an "X" denotes the time at which the subject took the product into the mouth. The data show that products containing 0.25% zinc salt or containing 0.5% zinc salt had malodor suppressing effect which extended far longer than the control was able to provide. These results are summarized in Table 1.

Figure 10:
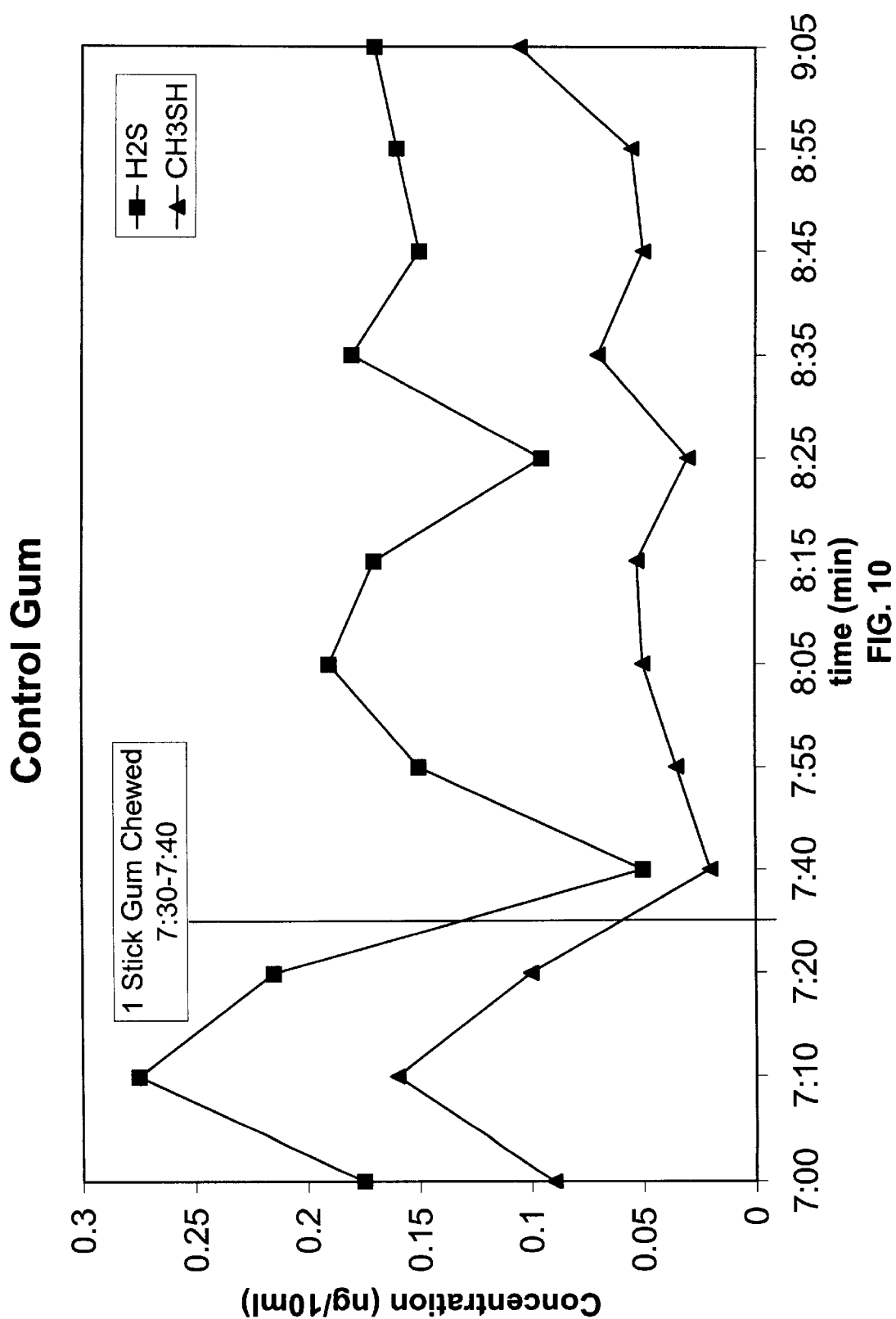
Figure 11:
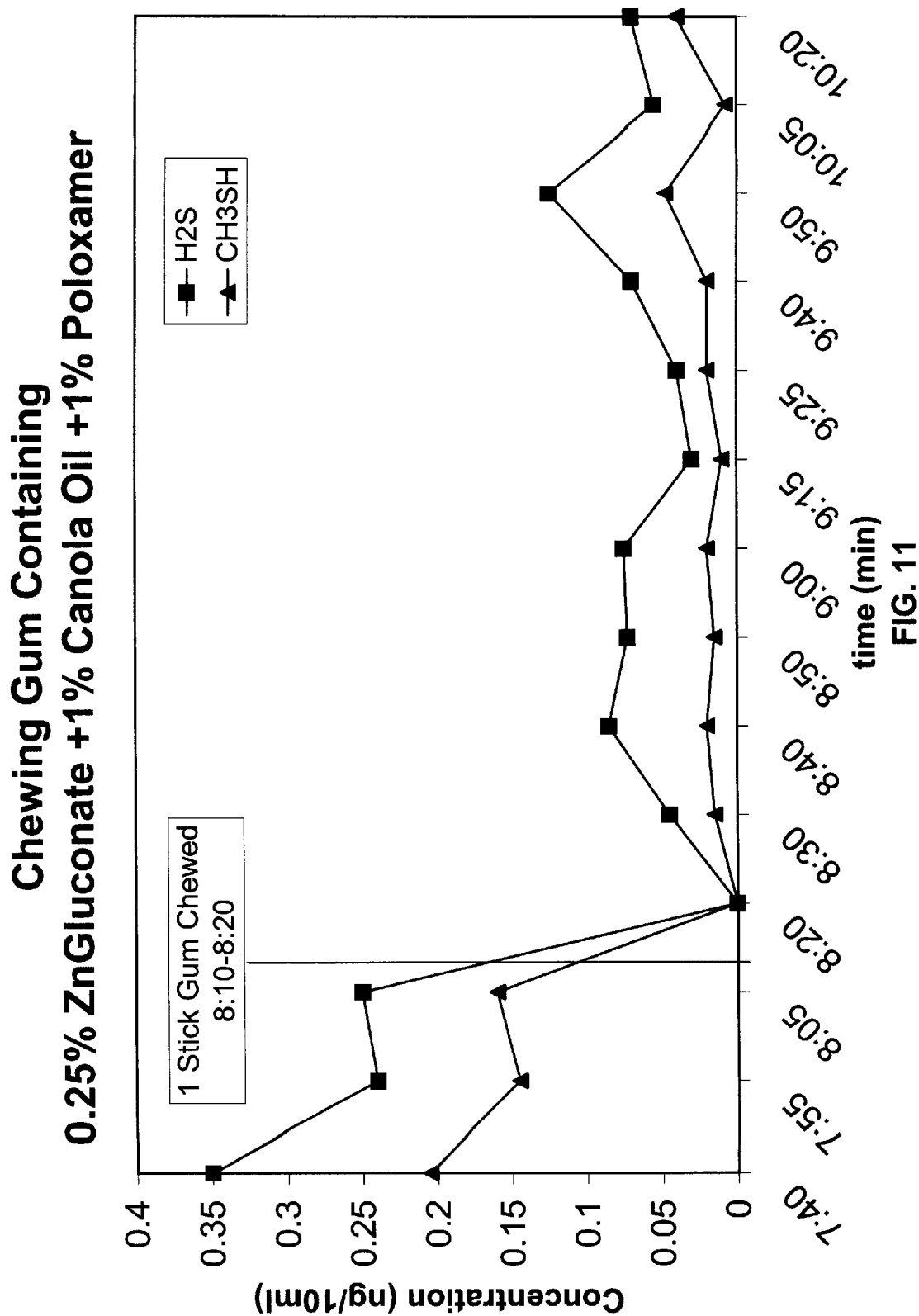
Figure 12:
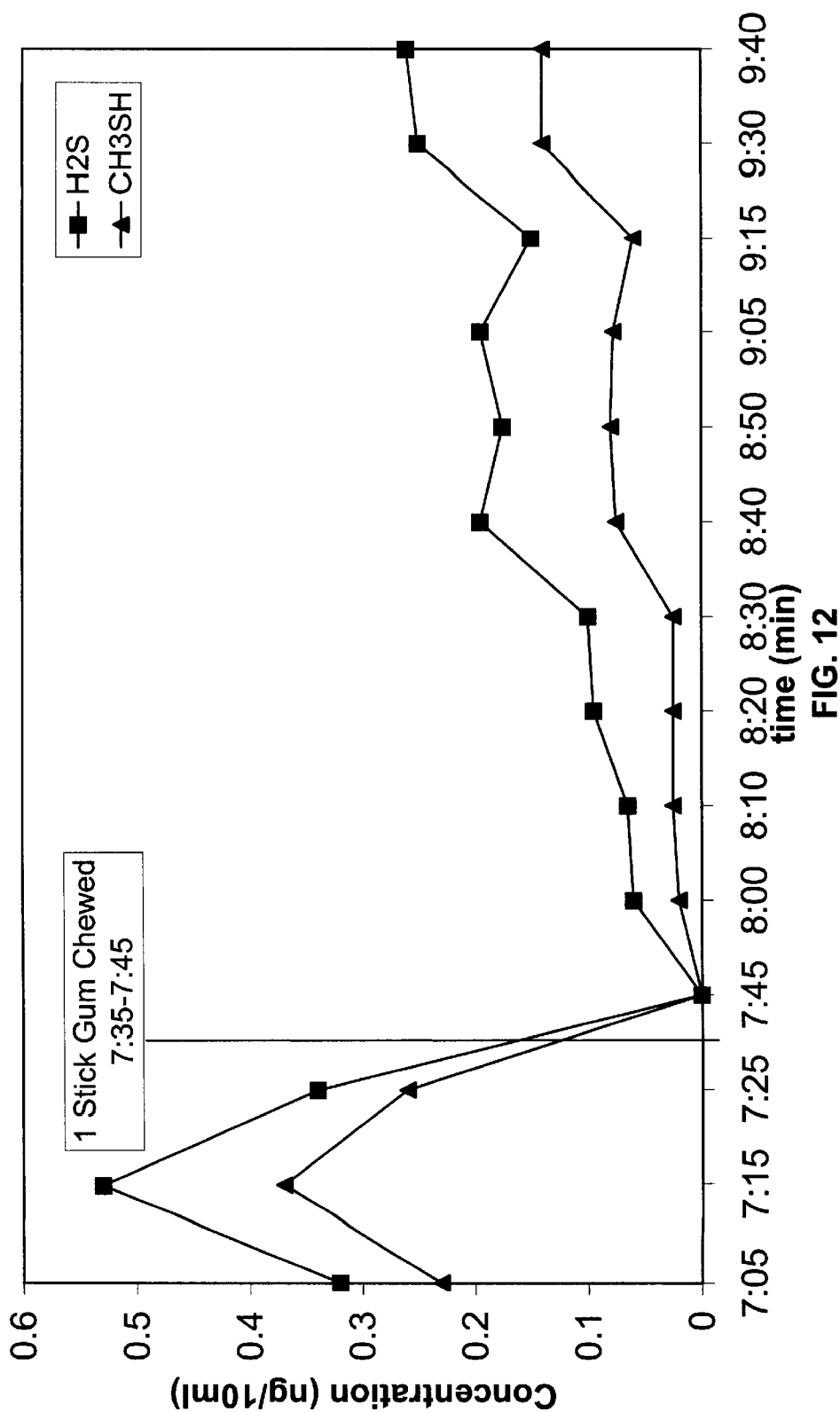
Figure 13:
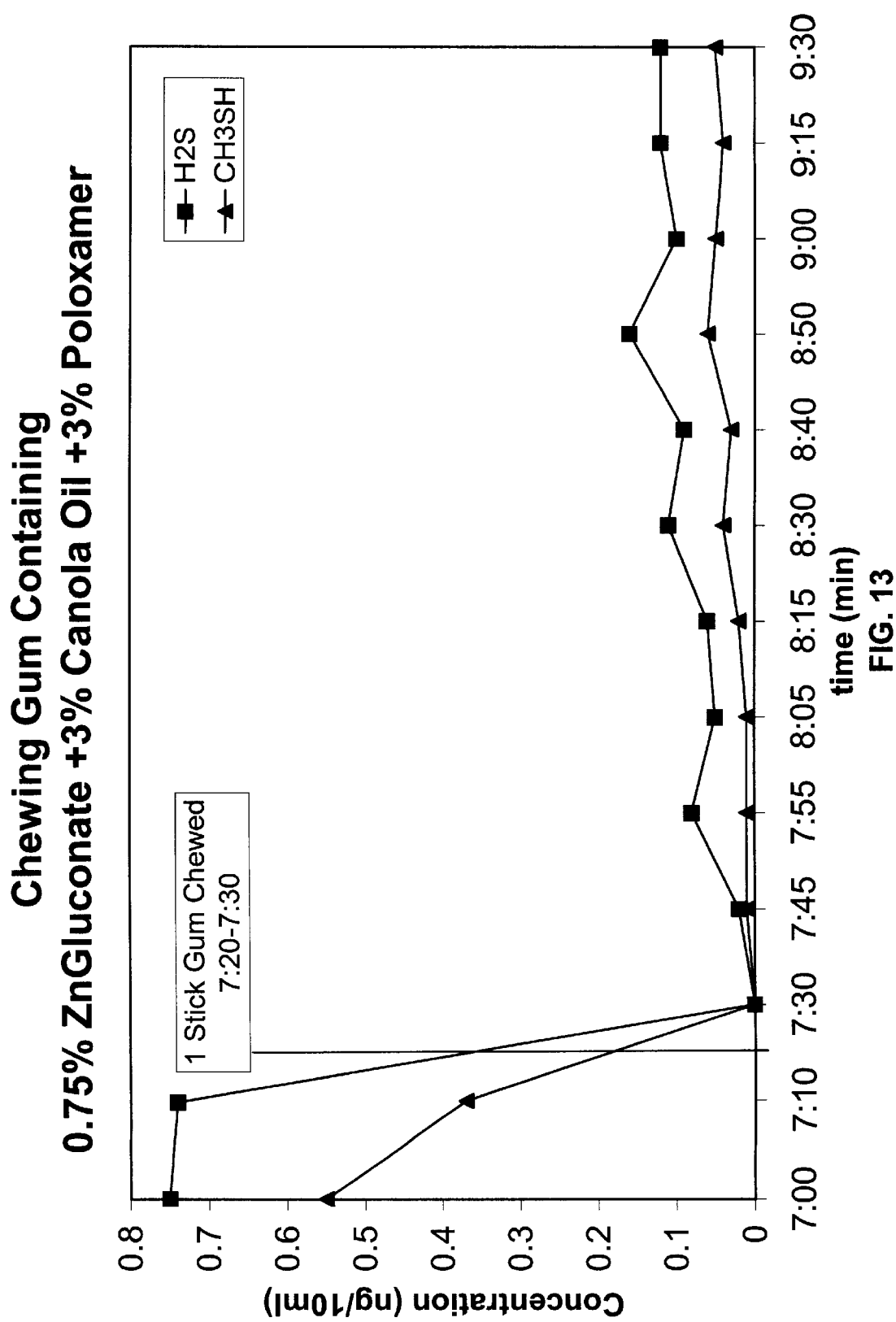

FIGS. 10 through 13 exhibit readings taken with a conventional chewing gum, both without the breath freshening composition of the present invention (seen as the control line in FIG. 10 and with the breath freshening composition of the present (FIGS. 11 through 13) invention, in varying amounts of the zinc salt, edible oil and nonionic surfactant. These results are summarized in Table II.

Again, it can be seen that comestibles containing the breath freshening composition of the present invention exhibit substantial, significant control of the $H_2S$ and $CH_3SH$ associated with malodor of the breath. Indeed, the $H_2S$ and $CH_3SH$ remained below the previous baseline levels for well over 2 hours, and essentially indefinitely, without showing an indication of returning to the baseline levels.

Figure 14:
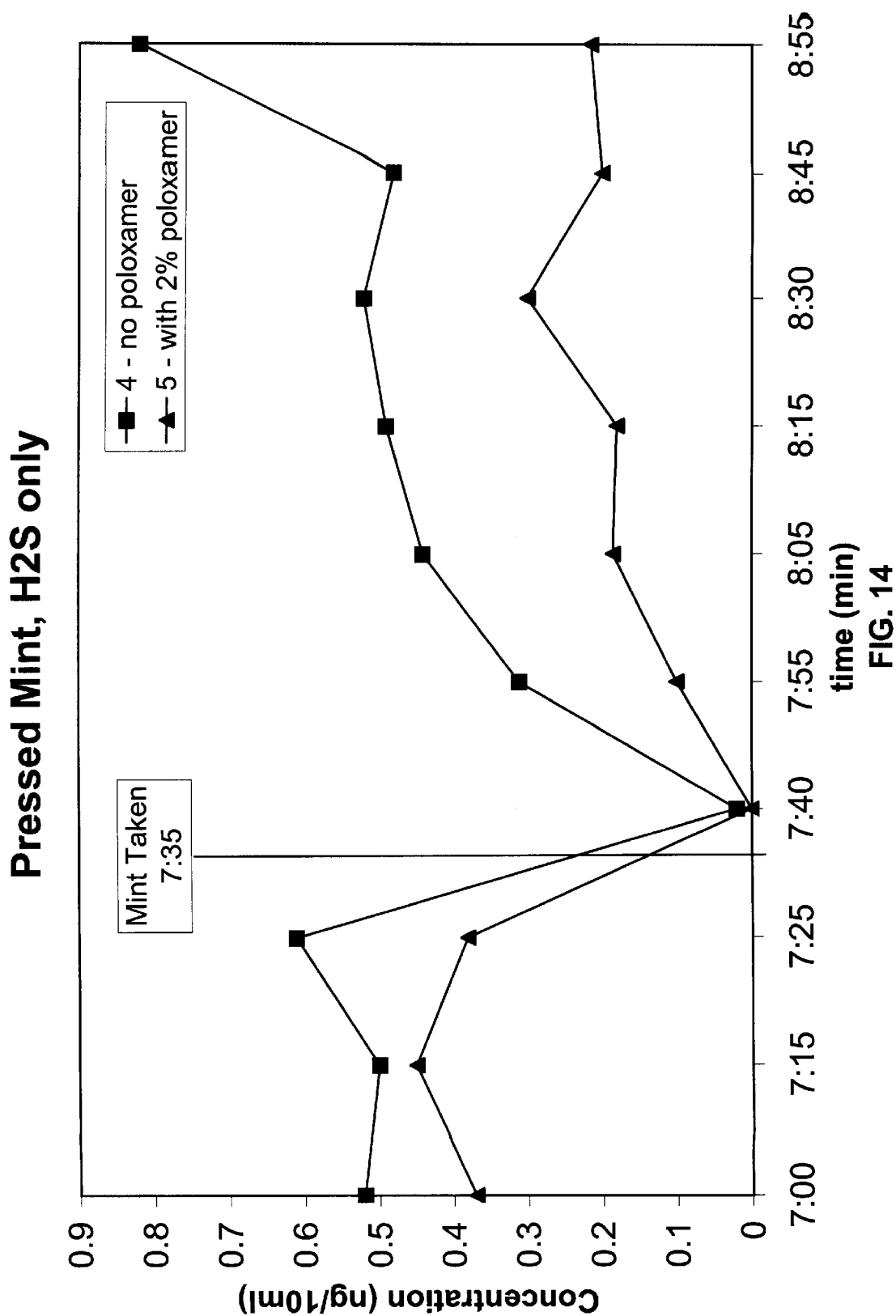
Figure 15:
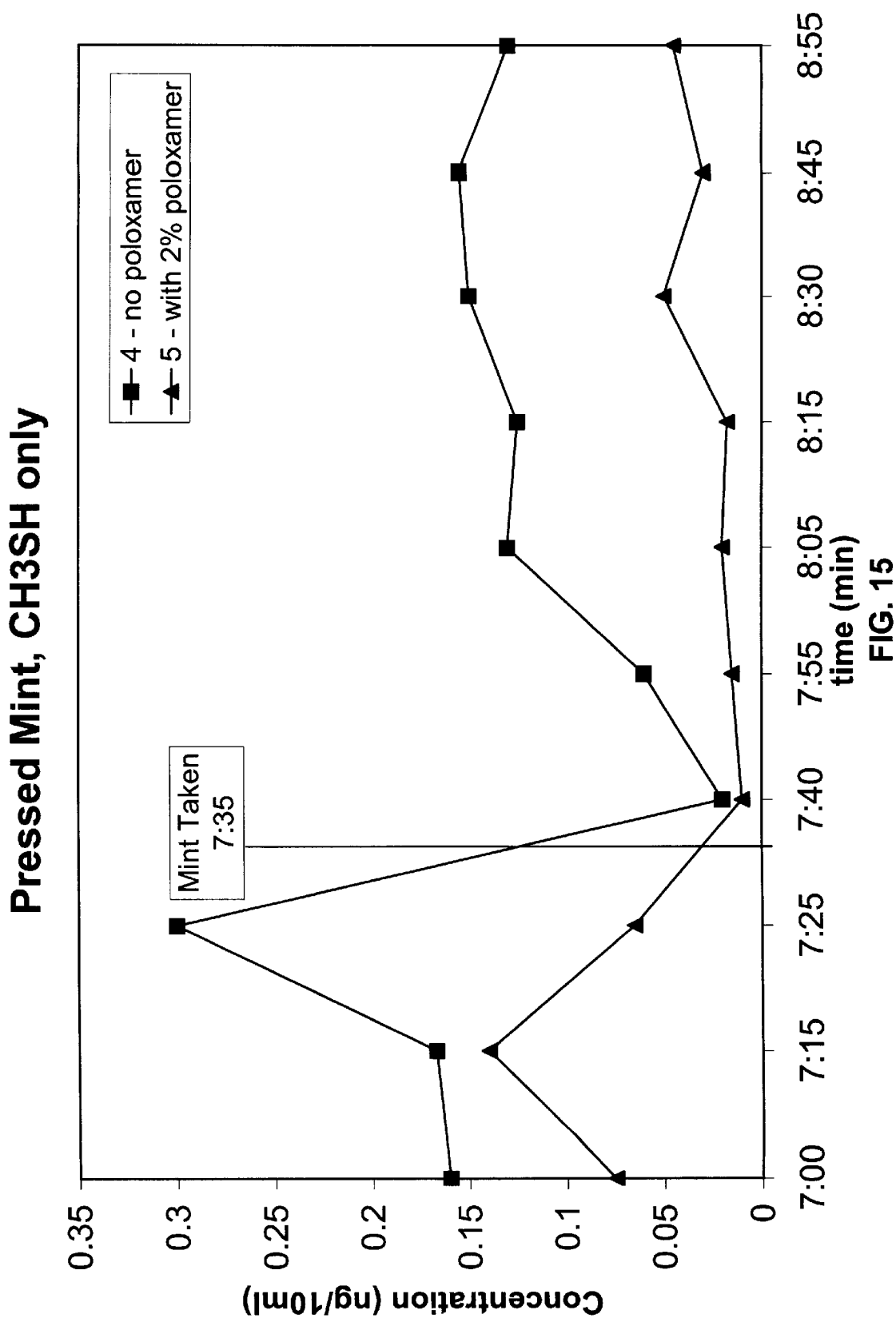
Figure 16:
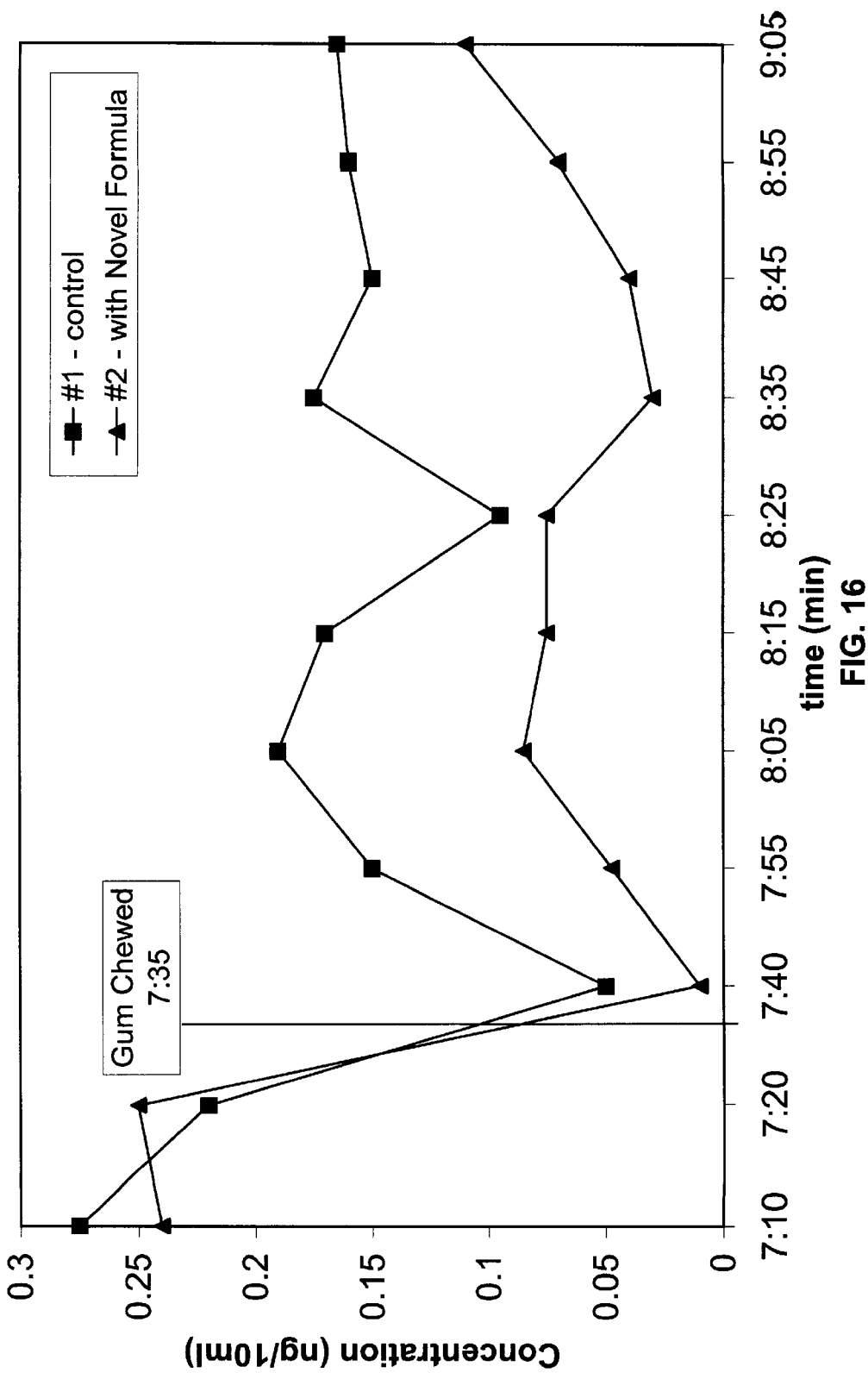

FIGS. 14 and 17 show the breath freshening (malodor control) effectiveness of comestible (pressed mints and gum) products with and without the nonionic surfactant. It can be seen that the surfactant significantly contributes to the malodor control provided by this invention. Thus, it is clear that the present invention represents not merely another zinc-based breath freshening product but a synergistic composition which provides improvement to an unexpected extent not previously attainable.

TABLE 1

| Composition of Additive | H₂S % Reduction | H₂S Time to Baseline | CH₃SH % Reduction | CH₃SH Time to Baseline |
|---|---|---|---|---|
| 0.25% Zn Glu + 0.5% Salatrim + 1% Poloxamer | 99% | 60 min | 69% | 60 min |
| 0.50% ZnGlu + 1% Salatrim + 2% Poloxamer | 99% | 90 min | 85% | 90 min |
| 0.25% ZnGlu + 0.5% Canola Oil + 1% Poloxamer | 99% | 60 min | 89% | 60 min |
| 0.50% ZnGlu + 1% Canola Oil + 2% Poloxamer | 99% | 60 min | 88% | 120 min |
| 0.25% ZnGlu + 2% Canola Oil + 2% Poloxamer | 96% | 90 min | 82% | 110 min |
| 0.25% ZnGlu + 2% Canola Oil + 1% Poloxamer | 99% | 65 min | 90% | 90 min |
| 0.5% ZnGlu + 2% Canola Oil + 1% Poloxamer | 99% | 75 min | 94% | 90 min |
| 0.50% ZnGlu + 2% Canola Oil + 2% Poloxamer | 99% | 120 min | 82% | 120 min |

We claim:

1. A breath freshening composition for humans consisting essentially of a divalent metal compound selected from the group consisting of physiologically acceptable zinc and copper compounds, an edible oil and a surfactant, said composition in the form of a tablet, a lozenge, a chewing gum or a pressed mint.

2. A composition according to claim 1 wherein the surfactant is a non-ionic surfactant selected from the group consisting of poly ($C_2$-$C_4$-alkoxy) esters of $C_{18}$-$C_{20}$ fatty acids, $C_4$-$C_{20}$ alkyl poly ($C_2$-$C_4$-alkoxy) esters of $C_8$-$C_{20}$ fatty acids, poly ($C_2$-$C_4$ alkoxy) esters of sorbitan, poly ($C_2$-$C_4$ alkoxylated)—$C_1$-$C_{20}$ alcohols, polyethylene glycols, and mixtures thereof.

3. A composition according to claim 1 wherein the surfactant is a polyoxypropylene-polyoxyethylene block co-polymer.

4. A composition according to claim 1 wherein the surfactant is a block copolymer of the formula:

$$HO-(CH_2CH_2O)_x-(CH(CH_3)CH_2O)_y-(CH_2CH_2O)_z-H$$

wherein x is 2–128, y is 16–67 and z is 2–128 and the copolymer has a molecular weight between 500 and 30,000.

5. A composition according to claim 1 wherein the divalent metal compound is selected from the group consisting of physiologically acceptable water soluble and sparingly water soluble organic and water insoluble inorganic zinc compounds.

6. A composition according to claim 5 wherein said zinc compound is selected from the group consisting of zinc gluconate and zinc lactate.

7. A composition according to claim 1 wherein said oil is selected from the group consisting of edible vegetable oils.

8. A composition according to claim 1 wherein said composition is in the form of a chewing gum further consisting essentially of a gum base, optional sweetening ingredient and optional flavoring ingredient.

9. A composition according to claim 8 wherein the surfactant is a polyoxypropylene-polyoxyethylene block co-polymer.

10. A composition according to claim 9 wherein said divalent metal compound is selected from the group consisting of zinc gluconate and zinc lactate.

11. A composition according to claim 8 wherein the surfactant is a block copolymer of the formula:

$$HO-(CH_2CH_2O)_x-(CH(CH_3)CH_2O)_y-(CH_2CH_2O)_z-H$$

wherein x is 2–128, y is 16–67 and z is 2–128 and the copolymer has a molecular weight between 1,000 and 30,000.

12. A composition according to claim 1 wherein said composition is in the form of a tablet, a lozenge or a dressed mint, said composition further consisting essentially of a water soluble polyhydric alcohol.

13. A composition according to claim 12 wherein said composition is in the form of a pressed mint.

14. A composition according to claim 12 wherein the surfactant is a block copolymer of the formula:

$$HO-(CH_2CH_2O)_x-(CH(CH_3)CH_2O)_y-(CH_2CH_2O)_z-H$$

wherein x is 2–128, y is 16–67 and z is 2–128 and the copolymer has a molecular weight between 1,000 and 30,000.

15. A composition according to claim 12 wherein the surfactant is a polyoxypropylene-polyoxyethylene block co-polymer.

* * * * *

UNITED STATES PATENT AND TRADEMARK OFFICE
CERTIFICATE OF CORRECTION

PATENT NO. : 6,030,605
DATED : February 29, 2000
INVENTOR(S) : Ronald P. D'Amelia It is certified that error appears in the above-identified patent and that said Letters Patent is hereby corrected as shown below:

<u>Title page,</u>
Item [75], "Ronald P. D'Ameila" should read -- Ronald P. D'Amelia --

Signed and Sealed this

Twenty-fourth Day of June, 2003

JAMES E. ROGAN
*Director of the United States Patent and Trademark Office*